United States Patent [19]

Vogel et al.

[11] 4,454,366
[45] Jun. 12, 1984

[54] METHOD OF RECOVERING AND RECYCLING BORON TRIFLUORIDE CATALYST

[75] Inventors: Roger F. Vogel, Jefferson Township, Butler County, Pa.; Ajay M. Madgavkar, Irvine, Calif.; Harold E. Swift, Gibsonia, Pa.

[73] Assignee: Gulf Research & Development Company, Pittsburgh, Pa.

[21] Appl. No.: 450,070

[22] Filed: Dec. 15, 1982

Related U.S. Application Data

[62] Division of Ser. No. 396,255, Jul. 8, 1982, Pat. No. 4,384,162.

[51] Int. Cl.$^3$ ............................. C07C 7/12; C07C 3/18
[52] U.S. Cl. ...................................... 585/525; 208/262; 208/291; 585/465; 585/472; 585/726; 585/823; 585/824; 585/830

[58] Field of Search ............... 585/465, 472, 473, 525, 585/726, 823, 824, 830; 208/262, 291

[56] References Cited

U.S. PATENT DOCUMENTS

| | | | |
|---|---|---|---|
| 4,213,001 | 7/1980 | Madgavkar et al. | 585/525 |
| 4,263,467 | 4/1981 | Madgavkar et al. | 585/525 |
| 4,300,006 | 11/1981 | Nelson | 585/525 |

*Primary Examiner*—Delbert E. Gantz
*Assistant Examiner*—A. Pal
*Attorney, Agent, or Firm*—Deane E. Keith; Forrest D. Stine; Donald L. Rose

[57] ABSTRACT

Spent boron trifluoride catalyst is removed from organic liquids by contacting the liquid with polyvinyl alcohol. For example, boron trifluoride catalyst is removed from 1-olefin oligomer product by passing the liquid oligomer through a bed of granular polyvinyl alcohol. The boron trifluoride is recovered from the polyvinyl alcohol and is recycled for use as a catalyst.

18 Claims, No Drawings

METHOD OF RECOVERING AND RECYCLING BORON TRIFLUORIDE CATALYST

This is a division, of application Ser. No. 396,255 filed July 8, 1982, now U.S. Pat. No. 4,384,162.

SUMMARY OF THE INVENTION

Boron trifluoride which is present in minor amounts as a spent catalyst in an organic liquid is removed from the organic liquid by contacting the liquid with particulate polyvinly alcohol. The boron trifluoride catalyst which is removed can be present in the organic liquid as dissolved boron trifluoride gas, or it can be coordinated with a polar compound, or it can be present in both forms. The boron trifluoride is recovered from the polyvinyl alcohol and is recycled for use as a catalyst.

DESCRIPTION OF THE INVENTION

Boron trifluoride is used as a catalyst in relatively small amounts in the synthesis of a wide variety of liquid organic compounds, and in particular liquid hydrocarbon compounds, including use as a catalyst in polymerizations, in alkylations, in esterifications, and the like. Depending on the particular reaction being catalyzed, boron trifluoride can be present in the reaction liquid either in the free state as dissolved boron trifluoride gas, or it can be in the form of a coordination compound. Additionally, it can be present in both forms, as a dissolved gas and also as part of a coordination compound. Once the catalyzed reaction is completed, this minor amount of boron trifluoride must be removed from the product organic liquid. But this removal presents costly processing and disposal problems.

These problems can be exemplified by the process in current use for the preparation of synthetic hydrocarbon functional fluids, such as synthetic lubricating oils, from higher 1-olefins, particularly 1-decene. In the process, as described in U.S. Pat. No. 4,045,507 for one, the 1-decene is oligomerized to a product predominating in the trimer and tetramer using a combination catalyst system comprising both free dissolved boron trifluoride gas and a coordination compound of boron trifluoride and a suitable polar compound such as n-butanol. The resulting oligomer product will contain both free dissolved boron trifluoride as well as the boron trifluoride coordination compound. This boron trifluoride must be removed from the oligomer product.

A typical processing scheme frequently recommended for eliminating boron trifluoride from the oligomer product includes the chemical destruction of the boron trifluoride by the addition of an aqueous caustic wash stream. But this procedure involves the loss of the relatively expensive boron trifluoride and further involves rather costly by-product handling and disposal procedures to avoid environmental contamination. The process also requires the removal of the introduced moisture from the hydrocarbon product. Furthermore, the n-butanol contaminant in the product must be separately removed and treated.

We have discovered a relatively inexpensive method for removing boron trifluoride, both the free, dissolved boron trifluoride and the boron trifluoride tied up in the coordination compound in an organic liquid. Our process is particularly beneficial, both for economical and for environmental reasons, because the separated boron trifluoride can be recycled for reuse in the process. As a result, both the boron trifluoride costs and the overall processing costs are substantially reduced. Additionally, any environmental problems currently resulting from catalyst by-product waste disposal are substantially eliminated.

Our invention comprises a hydrocarbon conversion process which utilizes boron trifluoride as a catalyst. In the process, a liquid hydrocarbon is reacted in the presence of boron trifluoride to form a liquid reaction product containing boron trifluoride. This liquid reaction product is contacted with polyvinyl alcohol whereby the polyvinyl alcohol adsorbs the boron trifluoride. The boron trifluoride is next desorbed from the polyvinyl alcohol and is recovered and is then recycled to the hydrocarbon conversion stage.

When the boron trifluoride is used in the free state, that is, not as a coordination compound, it is dissolved in the reaction liquid generally under moderate pressure. When the boron trifluoride is used as a coordination compound, it can be coordinated with a suitable polar compound in situ or it can be added to the reactor as the pre-reacted coordination compound. When the reactor is pressured with boron trifluoride in the presence of the coordinating polar compound, both dissolved, uncomplexed boron trifluoride and complexed boron trifluoride will be present in the reaction liquid. Various polar compounds have been recommended as useful for forming coordination compounds with boron trifluoride for use as a catalyst. These include: aliphatic ethers, such as dimethyl ether and diethyl ether; aliphatic alcohols, such as methanol, ethanol, n-butanol and decanol; polyols, such as ethylene glycol and glycerol; water; aliphatic carboxylic acids, such as acetic acid, propanoic acid and butyric acid; esters, such as ethyl acetate and methyl propionate; ketones, such as acetone; aldehydes, such as acetaldehyde and benzaldehyde and acid anhydrides, such as acetic acid anhydride and succinic acid anhydride.

The product from the boron trifluoride-catalyzed process, whether batch or continuous, will contain a significant, albeit minor, amount of the boron trifluoride catalyst, free and/or coordinated, which must be removed following reaction since it inherently contaminates the product. In general, it is desired that every product which is synthesized using boron trifluoride catalyst be essentially free of this substance. In general, boron trifluoride contaminant can be effectively removed from organic liquids by our process when it is present in an amount as high as about five to ten weight percent. More generally, boron trifluoride contaminant will be present in organic liquids in an amount between 0.005 and about one percent.

When uncomplexed boron trifluoride is present in a liquid in significant amounts, white fuming usually results upon exposure of the contaminated liquid to the atmosphere as the result of the reaction of the boron trifluoride vapors with atmospheric moisture. This fuming is a rough indicator of the presence of a significant quantity of undesired free boron trifluoride dissolved in the liquid.

The polyvinyl alcohol which we use in our process for removal of the boron trifluoride is present in particulate form, generally within a size range of between about 10 mm and about 400 mesh, and preferably within a range of about 10 mm and about 100 mesh. It can be used in a batch purification procedure in which the particles of polyvinyl alcohol are dispersed throughout the liquid product by agitation until the boron trifluoride is adsorbed by the polyvinyl alcohol. However, it is preferred to use a continuous separation procedure in which the reaction product is passed through a bed of granular polyvinyl alcohol. A cyclic operation is possible in which one bed of polyvinyl alcohol adsorbent is regenerated while a second bed is removing boron trifluoride contaminant from the product stream. Since polyvinyl alcohol is generally prepared by the hydrolysis of polyvinyl acetate, some residual acetate may be present. We prefer polyvinyl alcohol which is at least 80 percent hydrolyzed, and more preferably which is at least 85 percent hydrolyzed. We most prefer fully hydrolyzed polyvinyl alcohol.

A particularly fortuitous and advantageous discovery by us was that the polyvinyl alcohol removes not only free, dissolved boron trifluoride from the organic product liquid, but that it also removes boron trifluoride from its coordination compound with a polar compound, leaving the polar compound in the organic product liquid. Our data shows that polyvinyl alcohol is an effective adsorbent up to its saturation point for both dissolved and complexed boron trifluoride.

Our process for removing boron trifluoride contaminant from organic liquids can be conveniently carried out at room temperature (20°-25° C.) or lower, such as 0° C. Since elevated temperatures prevent the adsorption of the boron trifluoride by the polyvinyl alcohol, a temperature of about 100° C. is generally not exceeded in the adsorption process, and much lower temperatures are preferred.

In the adsorption process the organic liquid can suitably be passed through the bed of polyvinyl alcohol at a weight hourly space velocity in the range of about 0.1 to about 100 hr.$^{-1}$, preferably about 0.5 to about 20 hr.$^{-1}$, and most preferably about 1 to about 5 hr.$^{-1}$.

When the polyvinyl alcohol adsorbent is saturated with boron trifluoride, it is taken out of service. Desirably, the boron trifluoride is recovered from this adsorbent by extracting it, and the boron trifluoride and the adsorbent are reused. In a convenient procedure for the recovery of the boron trifluoride, the polyvinyl alcohol is heated at a moderate temperature, such as about 100° C. at a reduced pressure, to vaporize off the boron trifluoride. This recovered boron trifluoride can then be directly reused in the process. Alternatively, the boron trifluoride can be stripped from the polyvinyl alcohol adsorbent by contacting it with a polar compound. In this stripping procedure, the concentration of the polar compound will be high relative to the boron trifluoride. This recovery of boron trifluoride from the sorbent is possible because, it is believed, the distribution of the boron trifluoride between the phases is governed by equilibrium. For process simplification, the polar compound used in this recovery stage is the same one used in the catalytic coordination-compound catalyst.

It is also possible to coat a suitable solid support, such as silica, alumina, magnesia, zirconia, charcoal mixtures thereof such as silica-aluminas, and the like with polyvinyl alcohol for use as the adsorbent for boron trifluoride. This can be accomplished by contacting the support with a hot aqueous solution of the polyvinyl alcohol. The boron trifluoride can then be recovered from the saturated, supported polyvinyl alcohol for recycle. The regenerated supported polyvinyl alcohol can be directly used, or, if desired, the polyvinyl alcohol can be burned off and the support recoated with a fresh solution of polyvinyl alcohol for reuse.

DESCRIPTION OF PREFERRED EMBODIMENTS

DuPont Elvanol grade 70-05 polyvinyl alcohol was used in the following experiments. It was a low molecular weight, fully hydrolyzed (99-100 percent) composition of 40/50 mesh size. A liquid synthetic hydrocarbon oligomer mixture was produced from 1-decene by the process described in U.S. Pat. No. 4,045,507 using a boron trifluoride-n-butanol complex in a system pressured with boron trifluoride gas. The product mixture was therefore contaminated both with free and with complexed boron trifluoride. The boron in the purified product was analyzed using an atomic adsorption technique.

EXAMPLE 1

The ability of polyvinyl alcohol to adsorb boron trifluoride from a gas mixture was determined. A 13.1 g. sample of the polyvinyl alcohol was packed in a flow-through glass reactor. A gas mixture consisting of 100 cc/minute of nitrogen and 20 cc/minute of boron trifluoride was flowed through the polyvinyl alcohol at atmospheric pressure and room temperature (20°-25° C.). After 230 minutes the gas flow was stopped, and the polyvinyl alcohol adsorbent was weighed. It was found that the polyvinyl alcohol had adsorbed 16.4 g. of boron trifluoride, or 55.6 percent by weight.

EXAMPLE 2

A flow-through glass reactor was packed with a bed of 1.28 g. of the polyvinyl alcohol. Oligomer product contaminated with about 0.52 weight percent boron trifluoride was allowed to trickle down through the bed of adsorbent at a weight hourly space velocity of 11.5 hr.$^{-1}$ and at room temperature. Periodic cuts were collected about every thirty minutes, and some of these were analyzed for boron using atomic adsorption techniques. The boron trifluoride was almost quantitatively removed until the polyvinyl alcohol appeared to become saturated, at which point adsorption essentially stopped. When this breakthrough of substantial quantities of boron trifluoride in the product occurred, a total of about 73 g. of contaminated oligomer product had been processed, and a total of about 0.38 g. of boron trifluoride had been removed by the polyvinyl alcohol. The results of this experiment are set out in Table I.

TABLE I

| Cut No. | Wt., gms | Cumulative wt, gms. | B in cut, ppm | Total B removed mg. (est.) |
|---|---|---|---|---|
| 1 | 4.62 | 4.62 | — | 4.28 |
| 2 | 8.31 | 12.93 | <10 | 11.18 |
| 5 | 8.59 | 38.24 | 22 | 31.96 |
| 7 | 7.31 | 53.25 | 18 | 44.32 |
| 9 | 6.77 | 67.08 | 28 | 55.82 |
| 10 | 6.24 | 73.32 | — | 61.08 |
| 12 | 5.55 | 84.80 | 700 | 61.08 |

Several of these purified product cuts were analyzed by gas chromatography to determine whether the product itself suffered compositional changes as a result of the polyvinyl alcohol adsorption procedure. It was determined that there was no significant effect on the proportion of the various oligomer fractions, beyond normal analytical variation, as indicated from the results of the analysis as set out (in weight percent) in Table II.

TABLE II

| | $C_{10}$ | $C_{20}$ | $C_{30}$ | $C_{40}$ | $C_{50}{}^+$ |
|---|---|---|---|---|---|
| Crude product | 6.75 | 13.5 | 56.0 | 22.8 | 1.52 |
| Cut No. 1 | 4.58 | 11.1 | 56.7 | 24.4 | 3.24 |
| Cut No. 5 | 4.97 | 11.1 | 57.3 | 24.4 | 2.23 |
| Cut No. 9 | 4.42 | 11.4 | 57.5 | 24.6 | 2.08 |

EXAMPLE 3

A 1.64 gm. quantity of the polyvinyl alcohol adsorbent was placed in a glass column to form a bed about one-half inch in diameter and 1.5 inches high. The boron trifluoride-contaminated oligomer mixture containing 760 ppm of boron was pumped from a continuously stirred reactor through the adsorbent at a weight hourly space velocity of 46 hr.$^{-1}$ and at a temperature of 20°–25° C. Samples of decontaminated product were collected as before and were analyzed. The results, including the percent removal of the boron trifluoride, are shown in Table III.

TABLE III

| Sample | Total amount collected, gms | B in treated product, ppm | $BF_3$ removed, % |
|---|---|---|---|
| 1 | 14.76 | <5 | 99.34 |
| 2 | 45.10 | 10 | 98.68 |
| 3 | 107.42 | 19 | 97.50 |
| 4 | 154.16 | 41 | 94.61 |

The polyvinyl alcohol adsorption procedure was continued until a total of 185.3 gms. of the contaminated product were treated. Since the contaminated product prior to the polyvinyl alcohol adsorption treatment was determined, by analysis, to contain 3,280 ppm n-butanol, the 185.3 gms. of contaminated product, before treatment, contained 0.608 gm. of n-butanol. The polyvinyl alcohol was analyzed after treatment, and only 0.007 mg. of n-butanol was found on the polyvinyl alcohol.

In another experiment, a sample of polyvinyl alcohol adsorbent was subjected to five cycles of adsorption and regeneration using n-butanol. It was determined that the four-times regenerated polyvinyl alcohol was in effective adsorbent in the fifth cycle.

It is to be understood that the above disclosure is by way of specific example and that numerous modifications and variations are available to those of ordinary skill in the art without departing from the true spirit and scope of the invention.

What is claimed as the invention is:

1. A boron trifluoride-catalyzed chemical reaction which comprises the steps:
   (1) converting an organic reactant to an organic reaction product in a liquid-phase chemical reaction in the presence of boron trifluoride catalyst whereby a liquid-phase product solution is obtained containing said boron trifluoride;
   (2) contacting said liquid-phase product solution with a particulate polyvinyl alcohol composition whereby said boron trifluoride is adsorbed by the polyvinyl alcohol;
   (3) desorbing the boron trifluoride from the polyvinyl alcohol; and
   (4) recycling the desorbed boron trifluoride to the liquid-phase chemical reaction for further use as a catalyst.

2. A boron trifluoride-catalyzed chemical reaction in accordance with claim 1 in which the boron trifluoride catalyst comprises free dissolved boron trifluoride.

3. A boron trifluoride-catalyzed chemical reaction in accordance with claim 1 in which the boron trifluoride catalyst comprises a coordination compound of boron trifluoride and an organic polar compound.

4. A boron trifluoride-catalyzed chemical reaction in accordance with claim 1 in which the boron trifluoride catalyst comprises a coordination compound of boron trifluoride and water.

5. A boron trifluoride-catalyzed chemical reaction in accordance with claim 1 in which the polyvinyl alcohol is at least about 80 percent hydrolyzed.

6. A boron trifluoride-catalyzed chemical reaction in accordance with claim 1 in which the polyvinyl alcohol is of a particle size between about 400 mesh and about 10 mm.

7. A boron trifluoride-catalyzed chemical reaction in accordance with claim 1 in which said liquid-phase product solution is contacted with said particulate polyvinyl alcohol composition at a temperature between about 0° C. and about 100° C.

8. A boron trifluoride-catalyzed chemical reaction in accordance with claim 1 in which the polyvinyl alcohol is substantially fully hydrolyzed.

9. A boron trifluoride-catalyzed chemical reaction in accordance with claim 1 in which said liquid-phase product solution is substantially completely freed of boron trifluoride by adsorption of the boron trifluoride on said polyvinyl alcohol composition.

10. A boron trifluoride-catalyzed chemical reaction in accordance with claim 1 in which the boron trifluoride is desorbed from the said polyvinyl alcohol composition by contacting the polyvinyl alcohol composition with an organic polar compound whereby said boron trifluoride is desorbed and a coordination compound of said desorbed boron trifluoride and said organic polar compound is produced, and said coordination compound produced by the desorption procedure is recycled to the liquid-phase chemical reaction for use as a catalyst.

11. A boron trifluoride-catalyzed chemical reaction in accordance with claim 10 in which said organic polar compound is an alkyl alcohol having from one to about ten carbon atoms.

12. A boron trifluoride-catalyzed chemical reaction in accordance with claim 11 in which said organic polar compound is n-butanol.

13. A boron trifluoride-catalyzed chemical reaction in accordance with claim 1 in which the said organic reactant comprises a liquid hydrocarbon.

14. A boron trifluoride-catalyzed chemical reaction in accordance with claim 13 in which the said organic reactant comprises a liquid 1-olefin.

15. A boron trifluoride-catalyzed chemical reaction in accordance with claim 14 in which said organic reactant comprises 1-decene.

16. A boron trifluoride-catalyzed chemical reaction in accordance with claim 11 in which the said organic reactant comprises a liquid 1-olefin.

17. A boron trifluoride-catalyzed chemical reaction in accordance with claim 1 in which the boron trifluoride is desorbed from the said polyvinyl alcohol composition by vaporizing the boron trifluoride from the polyvinyl alcohol composition at a moderately elevated temperature.

18. A hydrocarbon conversion process which utilizes boron trifluoride as a catalyst which comprises the steps, reacting a liquid hydrocarbon in the presence of boron trifluoride to form a liquid reaction product containing boron trifluoride, contacting the reaction product with polyvinyl alcohol whereby said boron trifluoride is adsorbed by the polyvinyl alcohol, desorbing the boron trifluoride from said polyvinyl alcohol, and recycling the recovered boron trifluoride to the hydrocarbon conversion stage.

* * * * *